United States Patent [19]

Sakuma et al.

[11] Patent Number: 4,923,683

[45] Date of Patent: May 8, 1990

[54] COMPOSITIONS FOR PREVENTING TOOTH DECAY

[75] Inventors: Shuji Sakuma; Kiminori Atsumi, both of Chuo, Japan

[73] Assignee: Kabushiki Kaisha Sangi, Tokyo, Japan

[21] Appl. No.: 412,548

[22] Filed: Sep. 25, 1989

Related U.S. Application Data

[63] Continuation of Ser. No. 210,985, Jun. 24, 1988, abandoned.

[30] Foreign Application Priority Data

Jun. 27, 1987 [JP] Japan .................. 62-158831

[51] Int. Cl.$^5$ .................. A61K 7/16; A61K 7/18
[52] U.S. Cl. .................. 424/52; 424/57
[58] Field of Search .................. 424/52

[56] References Cited

U.S. PATENT DOCUMENTS

| | | | |
|---|---|---|---|
| 3,956,480 | 5/1976 | Dichter et al. | 424/49 |
| 3,957,964 | 5/1976 | Grimm | 424/49 |
| 4,166,606 | 3/1979 | Yamaga et al. | 424/52 |
| 4,177,258 | 12/1979 | Gaffar et al. | 424/52 |
| 4,183,915 | 1/1980 | Gaffar et al. | 424/52 |
| 4,203,966 | *5/1980 | Faunce | 424/52 |
| 4,265,877 | 5/1981 | Tenta | 424/52 |
| 4,292,306 | 9/1981 | Faunce | 424/52 |
| 4,327,079 | 4/1982 | Aokl | 424/57 |
| 4,342,741 | 8/1982 | Aokl | 424/57 |
| 4,348,381 | 9/1982 | Gaffar et al. | 424/52 |
| 4,357,317 | 11/1982 | Weyn et al. | 424/52 |
| 4,474,749 | 10/1984 | Kruppa | 424/52 |
| 4,634,589 | 1/1987 | Scheller | 424/49 |
| 4,767,615 | 8/1988 | Geho et al. | 424/49 |

FOREIGN PATENT DOCUMENTS 999238 11/1976 Canada.
1586915 3/1981 United Kingdom.

*Primary Examiner*—Shep K. Rose
*Attorney, Agent, or Firm*—Stevens, Davis, Miller & Mosher

[57] ABSTRACT

A tooth-decay preventing composition containing hydroxy-apatite and a fluoride, wherein at least one of the hydroxy-apatite and/or fluoride is microencapsulated or coated.

4 Claims, No Drawings

COMPOSITIONS FOR PREVENTING TOOTH DECAY

This application is a continuation of application Ser. No. 210,985, filed June 24, 1988 now abandoned.

BACKGROUND OF THE INVENTION

1. Field of the Invention

The present invention relates generally to a composition for preventing tooth decay, and more particularly to a tooth-decay preventing composition containing hydroxy-apatite and a fluoride, wherein at least either one or the hydroxy-apatite or fluoride is microencapsulated or coated, and moreover a tooth-decay preventing composition, wherein compositions containing hydroxy-apatite and a fluoride coexist in an unmixed state.

2. Description of the Prior Art

Fluorides are known to be effective in preventing tooth decay by virtue of such effects as strengthening of the enamel, suppression of the enzymatic action of bacteria which convert saccharides into acids, and suppression of the propagation of microorganisms relating to the corrosion destruction of enamel and dentine. Sodium fluoride, sodium monofluorophosphate, stannous fluoride and the like (hereinafter referred to simply as fluorides) are used for dentifrice compositions. However, to use a fluoride for dentifrice compositions in an amount sufficient to be really effective in preventing tooth decay is deemed by same as being impossible, since the amount of fluorine that can be incorporated in dentifrice compositions as fluoride is limited to 1,000 ppm or less, because of the toxicity of fluorine itself. Thus, the development of compositions sufficient to produce a decay preventive effect using an amount of fluorine within the set limits is still being awaited. On the other hand, hydroxy-apatite serves to absorb dental plaque responsible for tooth decay, while simultaneously it adheres to the surfaces of teeth, and thereby promoting the recalcification and strengthening of teeth. For this reason, hydroxy-apatite is added to dentifrice compositions as a satisfactory decay preventive. Accordingly, if a composition could be prepared containing hydroxy-apatite and a fluoride in such a way that they might exhibit a synergistic effect, then it would be expected that an ideal tooth-decay preventing composition could be obtained. However, it has been found that mixing of hydroxy-apatite with the fluoride causes easy conversion of hydroxy-apatite into apatite fluoride and calcium fluoride. Apatite fluoride and calcium fluoride fail to exhibit the decay-preventing action that the fluoride has, since they serve neither to absorb dental plaque nor recalcify and strengthen teeth. Besides, they are not absorbed onto the surfaces of teeth. Thus, although hydroxy-apatite and the fluoride are independently effective for the prevention of tooth decay, no tooth-decay preventing effect whatsoever is obtained with a composition wherein they exist together freely. For these reasons, a tooth-decaying preventing composition containing both the fluoride and hydroxy-apatite is not available in the prior art.

SUMMARY OF THE INVENTION

An object of the present invention is to provide a tooth-decay preventing composition which permits hydroxy-apatite and a fluoride to produce a synergistic effect upon the prevention of tooth decay, and which exhibits an improved fluorine effect as compared with the fluoride-containing compositions used theretofore in the prior art.

When simultaneously using dentifrice compositions which can deliver simultaneously hydroxy-apatite and a fluoride, hydroxy-apatite efficiently absorbs dental plaque and is adsorbed onto the surface layer or enamel in an extremely remarkable manner. The adsorbed hydroxy-apatite is recalcified on the surface layer of teeth, and the recalcified hydroxy-apatite is efficiently changed to apatite fluoride by the fluorine that has been coexisting with the hydroxy-apatite. Hence, the surfaces of the teeth are applied with a fresh coating of apatite fluoride which exhibits the tooth-decay preventing effect of fluorine. In addition, it has been noted that the effect of utilizing a fluorine in this way is considerably enhanced, as compared with the amount of fluorine that can be carried onto the surfaces of teeth from the conventional tooth-decay preventing compositions containing the fluoride alone. In the case of the conventional tooth-decay preventing compositons containing the fluoride alone, it was considered that they should contain at least 500 ppm of fluorine in order to make effective use of the fluorine. However, it has now been found that if the fluoride is allowed or made capable to exist together with hydroxy-apatite, then a fluorine effect equivalent to that of compositions containing fluorine in an amount of 500 ppm or more can be expected in a fluorine content of 100 ppm or less. The present invention has been made on the basis of such findings.

As already mentioned, previously upon being blended together, the fluoride and hydroxy-apatite yield apatite fluoride, calcium fluoride, etc. too easily and hinder the beneficial effect of hydroxy-apatite. In expectation of the synergistic effect of the fluoride and hydroxy-apatite, therefore, the present inventors have devised a method wherein a fluorine-containing tooth-decay preventing composition and hydroxy-apatite-containing composition are separately prepared, and, in delivery, they are measured out in predetermined amounts without admixing and are admixed just prior to use or in the mouth. More specifically, according to this method, the fluoride- and hydroxy-apatite-containing compositions are designed to be separately stored in receptacles isolated from each other and admixed together at the time of use. It has further been found that the fluoride and hydroxy-apatite can coexist stably in a single composition by microencapsulating or coating at least one of the fluoride or hydroxy-apatite. In other words, the present invention provides a tooth-decay preventing composition in which hydroxy-apatite and fluoride are allowed to coexist stably, and which is used in such a manner that the fluoride and hydroxy-apatite are mixed together just prior to use or in the mouth, or otherwise designed in such a manner that at least one of the fluoride and hydroxy-apatite is coated or microencapsulated, whereby the coatings or microcapsules are broken up or ruptured to cause the fluoride and hydroxy-apatite to produce a synergistic effect upon which the prevention of tooth decay can be expected.

Coating materials used for the preparation of the coated hydroxy-apatite or fluoride may easily be selected from any conventional coating materials from pharmaceuticals depending upon the pH of the tooth-decay preventing compositions. Coating materials soluble in the intestines are selected when their pH is weakly acidic and coating materials soluble in the stomach when their pH is weakly alkaline. However, hydroxy-apatite has an adsorbability so strong that polar substances such as proteins, amino acids and fatty acids are adsorbed thereon. Once hydroxy-apatite has such a polar substance adsorbed thereon, both its adsorbability with respect to the dental plaque and its adherence with respect to the surfaces of teeth decrease, resulting in a decline in its tooth-decay preventing effect. Accordingly, when a substance of strong polarity is used as the coating material, the tooth-decay preventing effect of hydroxy-apatite is lessened, since it is adsorbed onto the hydroxy-apatite. During its long-term storage, a coating material of strong polarity may swell in moisture and be permeated by such moisture to bring hydroxy-apatite into contact with the fluoride, thereby forming apatite fluoride. Hence, the coating material selected for use should have as low a polarity as possible and be as difficult to swell in moisture as possible. Preferably, the coating materials used include shellac; waxes; fats; vinylpyridine, alkyl vinylpyridine and polymers/copolymers of other vinyl monomers; ethyl cellulose, benzyl cellulose, cellulose acetobutyrate and other cellulose derivatives; polyvinyl acetal diethylaminoacetate and dimethylaminoethyl methacrylate/methyl methacrylate co-polymers; and so on.

The coated hydroxy-apatite or fluoride may easily be obtained for example by treating synthetic hydroxy-apatite finely separated to between 1 to 20 um; with particles or granules of the fluoride heretofore used as an oral hygienic material such sodium fluoride, sodium monofluorophosphate or stannous fluoride; or calcium carbonate, sodium hydrogen phosphate or other tooth powders on which these fluorides are carried with a coating material-containing solution in the conventional manner. For example, 10 kg of hydroxy-apatite finely divided and sieved to 20 um or less is loaded on a coating pan. While the pan is being rotated, it is sprayed with a solution of the coating material diethylamonoacetyl polyvinyl acetal in a ten-fold amount of a mixed methanol/acetone solution (50:50 weight %). In the meantime, hot air is supplied to the pan to volatize the solvent. The amount of coating material used should be in a range of 3 to 10%, preferably 5 to 10%, with respect to the hydroxy-apatite amount. The fluoride may also be coated in a manner similar to that described above.

For the preparation of the microencapsulated hydroxy-apatite or fluoride, it is convenient to use as the polymer, ethyl cellulose, benzyl cellulose, cellulose acetobutyrate, polyethylene, polyvinyl chloride, rubber, polyvinyl acetate or the like and to separate a polymer phase from an organic solution system. A suspension of hydroxy-apatite or an aqueous solution of the fluoride is emulsified or dispersed in a solution of the polymer as mentioned above in the presence of an emulsifier, and a non-solvent for the polymer that is miscible with the solvent, is added under agitation to the resulting emulsion or dispersion to precipitate a concentrated amount of polymer liquid in a form surrounding the emulsified and dispersed matter acting as a core, thereby obtaining the desired product in the form of microcapsules. For instance, 100 parts of a 5% aqueous solution of sodium fluoride are emulsified and dispersed in 400 parts of a solution of 5% of ethyl cellulose dissolved in a 1:1 mixed xylene/carbon tetrachloride solution, using as the emulsifier Turkey red oil dissolved in a 1% aqueous phase. Added to this dispersion are 400 parts of carbon tetrachloride, and the resulting dispersion is diluted as a whole. Afterwards, 1200 parts of petroleum ether are added dropwise to the diluted product while stirring. Ethyl cellulose then precipitates around a water droplet for capsulation. The capsulating suspension is decanted to remove the supernatant liquid and is washed several times with a 2:1 mixed petroleum ether/carbon tetrachloride solution. Subsequent drying by spray drier provides microcapsules. In a manner similar to that mentioned above, microencapsulated hydroxy-apatite may be obtained from a hydroxy-apatite suspension. For use, the thus obtained microencapsulated or coated fluoride may be quantitatively determined in the conventional manner.

The thus obtained coated or microencapsulated hydroxy-apatite or fluoride may be blended with tooth-decay preventing compositions in the conventional manner. It is understood that the "tooth-decay preventing compositions" refer to those used for the prevention of tooth decay in oral hygiene, and include dentifrices in the form of tooth powder, oil and paste, chewing gum, troches, gargles and so on.

The coated or microencapsulated hydroxy-apatite or fluoride is physically and chemically stable, and may easily be blended with dentifrices, chewing gum and the like. Up to now, hydroxy-apatite and fluorides have been blended with dentifrices respectively. For the preparation of dentifrices containing the coated or microencapsulated hydroxy-apatite or fluoride, therefore, all or a part of the hydroxy-apatite, polishing powder and fluoride contained in the dentifrices used heretofore in the prior art may be replaced as required by the coated or microencapsulated hydroxy-apatite or fluoride. Alternatively, the coated or microencapsulated hydroxy-apatite or fluoride may be added to the existing dentifrices. Thus, dentifrices wherein the fluoride and hydroxy-apatite exist together may easily be prepared according to the known manner. Chewing gum comprises a main gum ingredient such as vinyl acetate resin, ester gum, chicle or polyisobutylene and further includes a plasticizer such as methyl acetylrecinoleate, wax, polyisobutene or BpBG and an improver such as calcium or talc. If the improver is wholly or partially replaced by the coated or microencapsulated hydroxy-apatite or fluoride, it will then be possible to easily obtain chewing gum, wherein the fluoride and hydroxy-apatite coexist, by an ordinary available production method.

With the tooth-decay preventing composition of the present invention containing both hydroxy-apatite and fluoride wherein the compositions containing hydroxy-apatite and fluoride are placed in separate receptacles in which they do not admix while in preservation, or wherein at least one of the hydroxy-apatite and the fluoride is coated or microencapsulated, it is very unlikely that hydroxy-apatite will come into direct contact with the fluoride and change to apatite fluoride or calcium fluoride during preservation. The fluoride and hydroxy-apatite are mixed together at the time of use or, if coated or microencapsulated, are broken up or ruptured by brushing or mastication to exhibit their tooth-decay preventing effects.

DESCRIPTION OF THE PREFERRED EMBODIMENT

The present invention will now be explained with reference to examples. It is understood, however, that the coated hydroxy-apatite and fluoride used are hydroxy-apatite (of 1 to 20 um) and calcium carbonate carried on sodium fluoride, each coated with 7% by weight of diethylaminoacetyl polyvinyl acetal, and that the microencapsulated sodium fluoride refers to one microencapsulated with ethyl cellulose. It is also understood that the results of analysis indicated that the coated fluoride contained 5.0% by weight of sodium fluoride and the microencapsulated sodium fluoride 3.6% by weight of sodium fluoride.

EXAMPLE 1

| | |
|---|---|
| Sodium pyrophosphate | 20% |
| Coated hydroxy-apatite | 22.0% |
| Glycerin | 15.0% |
| Sorbitol 70% | 10.0% |
| Na-CMC | 1.4% |
| Stannous fluoride | 1.5% |
| Perfume | 1.0% |
| Saccharin sodium | 0.2% |
| Sodium lauryl sulfate | 2.0% |
| Butyl p-oxybenzoate | 0.1% |
| Water | 26.8% |
| Total | 100.0% |

EXAMPLE 2

| | |
|---|---|
| Calcium carbonate | 20.0% |
| Dibasic calcium phosphate | 20.0% |
| Coated hydroxy-apatite | 40.0% |
| Calcium pyrophosphate | 10.0% |
| Glycerin | 1.0% |
| Propylene glycol | 1.0% |
| Ethyl p-oxybenzoate | 0.1% |
| Capsulated sodium fluoride | 0.1% |
| Perfume | 1.20% |
| Saccharin sodium | 0.10% |
| Sodium lauryl sulfate | 0.70% |
| Water | 5.20% |
| Total | 100.0% |

EXAMPLE 3

| | Hydroxy-apatite-containing composition | Fluoride-containing composition |
|---|---|---|
| Aluminium hydroxide | 30.0% | 40.0% |
| Hydroxy-apatite | 10.0 | — |
| Carboxy-methyl cellulose | 1.3 | 1.3 |
| Sorbitol | 19.0 | 19.0 |
| Propylene glycol | 2.0 | 2.0 |
| Sodium lauryl sulfate | 1.0 | 1.0 |
| Saccharin-sodium | 1.0 | 1.0 |
| Sodium fluoride | — | 0.01 |
| Perfume | 1.1 | 1.1 |
| Ethyl p-oxybenzoate | 0.005 | 0.005 |
| Water | 34.595 | 34.585 |
| Total | 100.000 | 100.000 |

EXAMPLE 4

| | Hydroxy-apatite-containing composition (Powder) | Fluoride-containing composition (Paste) |
|---|---|---|
| Amorphous silica | — | 20.0 g |
| Hydroxy-apatite | 1.0 g | — |
| Propylene glycol | — | 2.0 |
| Glycerin | 0.01 g | 19.0 |
| Carboxy-methyl cellulose | — | 1.2 |
| Sodium lauryl sulfate | — | 1.0 |
| Saccharin-sodium | — | 0.9 |
| Butyl p-oxybenzoate | 0.001 g | 0.005 |
| Sodium monofluorophosphate | — | 0.7 |
| Perfume | — | 1.0 |
| Water | — | 54.195 |
| Total | 1.011 g | 100.0 g |

EXAMPLE 5

Chewing Gum

| | |
|---|---|
| Vinyl acetate resin | 64.5% |
| Polyisobutylen | 5.0 |
| Methyl acetylrecinoleate | 10.0 |
| Ester gum | 5.0 |
| Coated fluoride | 0.5 |
| Hydroxy-apatite | 10.5 |
| Sweetener | Suitable Amount |

In the tooth-decay preventing composition of the invention containing hydroxy-apatite and fluoride wherein separate compositions containing hydroxy-apatite and fluoride are placed in separate receptacles in which they are not admixed during preservation, or wherein at least one of the hydroxy-apatite and fluoride is coated or microencapsulated, it is very unlikely that hydroxy-apatite will contact and react with the fluoride during preservation, yielding apatite fluoride. Hence, the present composition can withstand preservation over an extended period of time. The hydroxy-apatite and fluoride are mixed together at the time of use or, if coated or micoencapsulated, are broken up or ruptured to permit their individual tooth-decay preventing effects yet so synergistically that they are much more effective than hydroxy-apatite or fluoride alone. In addition, the effect of the fluoride is enhanced by the presence of hydroxy-apatite. Thus, the present composition allows the fluoride to exhibit its maximum tooth-decay preventing effect, as compared with the conventional fluoride-containing tooth-decay preventing composition, and makes possible a reduction in the content of fluoride. This means that fluorine can be expected to have considerable effect upon the prevention of tooth decay with use of fluorine in an amount much below the set limits.

What is claimed is:

1. In the art of coating teeth with an effective tooth decay preventing amount of fluoride in a dentifrice containing hydroxy-apatite which serves to absorb dental plaque responsible for tooth decay which simultaneously adheres to the surface of teeth, the improvement wherein the premature reaction of hydroxy-apatite with fluoride which yields apatite fluoride acid calcium fluoride is avoided which consists essentially of the step of breaking or rupturing of coated hydroxy-apatite or microencapsulated hydroxy-apatite at time of use in a hydroxy-apatite containing fluoride dentifrice thereby promoting recalcification and strengthening of teeth.

2. The method according to claim 1, wherein the fluoride is sodium fluoride, sodium monofluorophosphate, or stannous hydroxy-apatite fluoride.

3. The method according to claim 1, wherein the coating includes a coating material of shellac; waxes; fats; vinylpyridine, alkyl vinylpyridine and polymers/copolymers or other vinyl monomers; ethyl cellulose, benzyl cellulose, cellulose acetobutyrate; polyvinyl acetal diethylaminoacetate and dimethylaminoethyl methacrylate/methyl or methacrylate copolymers.

4. The method according to claim 1, wherein the coating material for the microencapsulation is a polymer of ethyl cellulose, benzyl cellulose, cellulose acetobutyrate, polyethylene, polyvinyl chloride, rubber, or polyvinyl acetate.

* * * * *